United States Patent [19]

Sharp et al.

[11] 4,068,664

[45] * Jan. 17, 1978

[54] SURGICAL SUCTION WAND ASSEMBLY AND METHOD

[75] Inventors: Russell G. Sharp, Sugar Land; Charles C. Reed; Denton A. Cooley, both of Houston, all of Tex.

[73] Assignee: Texas Medical Products, Inc., Houston, Tex.

[*] Notice: The portion of the term of this patent subsequent to June 15, 1993, has been disclaimed.

[21] Appl. No.: 661,224

[22] Filed: Feb. 25, 1976

[51] Int. Cl.² .............................................. A61M 1/00
[52] U.S. Cl. .............................. 128/276; 128/350 R; 128/240; 32/33
[58] Field of Search .............................. 128/275–278, 128/239, 240, 350 R; 32/33

[56] References Cited

U.S. PATENT DOCUMENTS

| 2,742,701 | 4/1956 | Berger | 32/33 |
| 3,136,316 | 6/1964 | Beall | 128/350 R |
| 3,426,759 | 2/1969 | Smith | 128/276 |
| 3,528,427 | 9/1970 | Sheridan | 128/276 |
| 3,958,573 | 5/1976 | Wiley | 128/276 |
| 3,963,028 | 6/1976 | Cooley et al. | 128/276 |

*Primary Examiner*—Robert W. Michell
*Assistant Examiner*—Henry S. Layton
*Attorney, Agent, or Firm*—H. Ross Workman; J. Winslow Young

[57] ABSTRACT

The disclosed surgical suction wand assembly and method includes a modular suction wand including a hollow suction tip the interior of which has a square or other suitable polygonal cross-sectional configuration which substantially improves the precision and facility with which apertures may be formed in the suction tip. The tip may be provided with an elongated interiorly disposed tube simultaneously providing for effective aspiration of small amounts of liquid as well as a large suction area for efficiently aspirating larger volumes with minimal opportunity for obstruction. The suction tip is provided with a coupling device adapted to receive any one of a plurality of adaptor configurations constructed so as to increase the versatility of the suction tip without requiring large numbers of separate forming molds.

2 Claims, 9 Drawing Figures

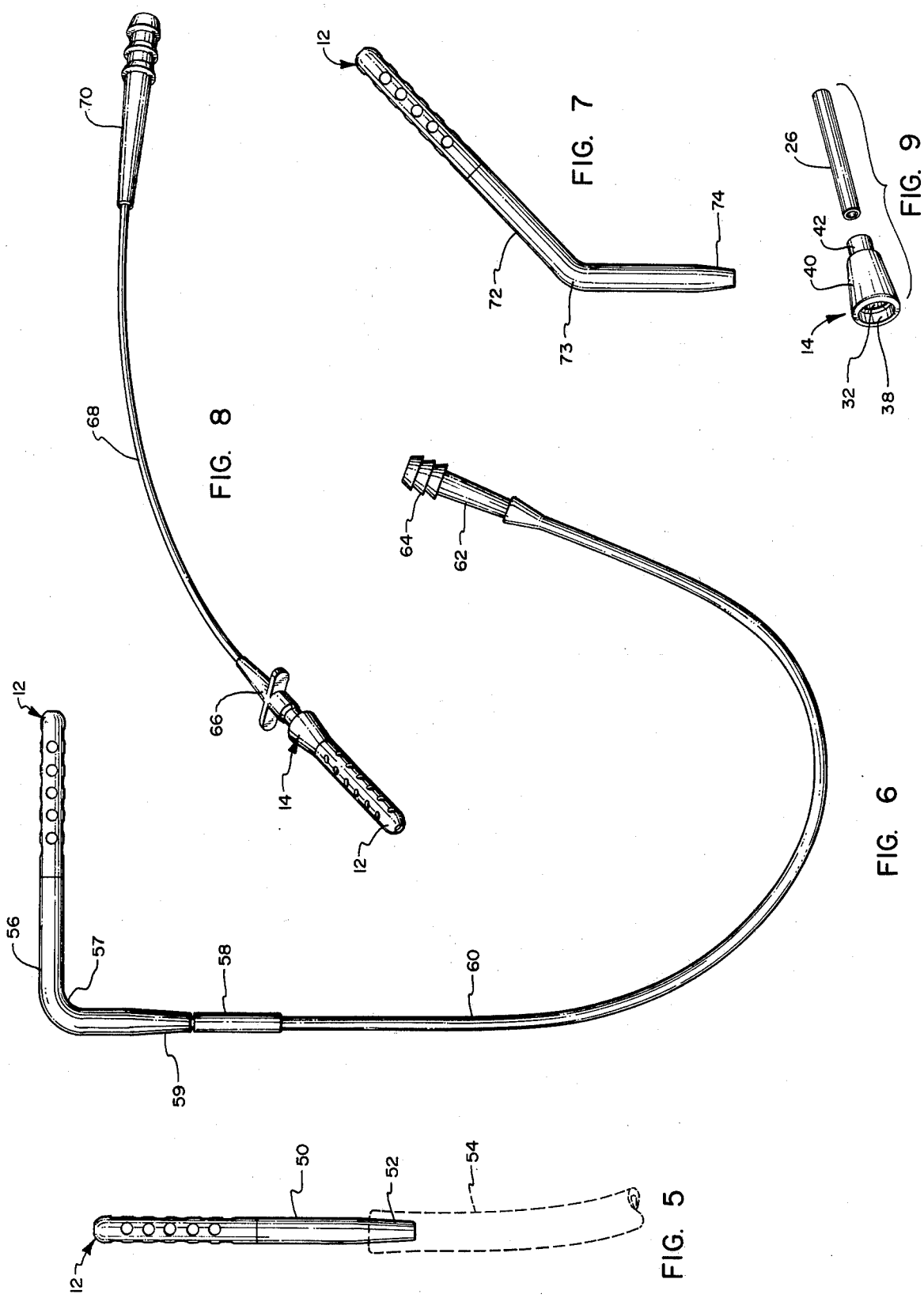

SURGICAL SUCTION WAND ASSEMBLY AND METHOD

BACKGROUND

1. Field of the Invention

This invention relates to improvements in surgical suction wands and more particularly to a surgical aspiration wand assembly and method for removing blood and other fluids from a surgical field.

2. The Prior Art

Aspirator devices are commonly used in surgical procedures for a wide variety of applications. Examples of suitable applications include open-heart surgery, to clear hemothorax and serous fluid in the abdominal cavity (ascites). Examples of prior art devices include U.S. Pat. Nos. 3,109,426 and 3,191,600 and German Pat. No. 1,491,755.

It is typical of the prior art devices to provide a suction wand with one or more openings immediately at the tip of the wand for aspirating fluids. However, historically suction devices have been easily clogged by bits of tissue and other matter in the surgical fields. Small amounts of tissue can easily clog the small area defining the aspiration port of the prior art devices. Moreover, substantial vacuum over a small number of aspiration ports can easily cause tissue trauma to connected tissue against which the aspiration port is inadvertently urged. It is also desirable to provide surgical suction assemblies having a variety of configurations, depending upon the particular type of surgical procedure engaged in. For example, in some procedures a straight suction tip is preferred. In others, a suction tip with a noticeable bend or an elongated handle are desired. Historically, each suction wand configuration has been separately manufactured at considerable expense.

It would, therefore, be an advancement in the art to provide a surgical suction assembly and method which readily accommodates fabrication of a wide variety of suction devices from a small number of modular parts and which, when assembled, can efficiently aspirate fluids in small or large amounts without tissue trauma. Such a system and method is disclosed herein.

BRIEF SUMMARY AND OBJECTS OF THE INVENTION

The present invention is a surgical suction wand assembly which is assembled from two basic modular parts: (1) a hollow perforated tip and (2) an adaptor for the tip. All fittings are standardized to readily accommodate interchangeability of the tip with variously configurated adaptors. Accordingly, a wide variety of suction wand configurations may be prepared for a relatively few modular parts. The parts are inexpensively fabricated and may be bonded together by chemical adhesive or sonic weld. A hollow suction tube is mounted coaxially and in spaced relationship inside the perforated tip so as to permit fluid aspiration with maximum efficiency even in the presence of tissue fragments and small volumes of fluid.

It is therefore a primary object of the present invention to provide an improved surgical suction wand assembly and method.

Another valuable object of the present invention is to provide a surgical suction wand assembly having standardized couplings for a suction tip and a variety of adaptors, each adaptor having a different configuration.

It is another object of the present invention to provide a surgical suction wand assembly which may be readily assembled from a relatively small number of modular components to thereby provide a variety of suction wand configurations.

A further object of the present invention is to provide an improved method of assemblying a suction wand.

It is another important object of the present invention to provide a suction tip which efficiently aspirates small or large volumes of body fluids even in the presence of tissue fragments and with minimum tissue trauma.

These and other objects and features of the present invention will become more fully apparent from the following description and appended claims taken in conjunction with the accompanying drawing.

BRIEF DESCRIPTION OF THE DRAWING

FIGS. 5-8 represent perspective elevational views of various adaptor configurations usable with the suction tip of the present invention, each of the adaptors having a different overall configuration; and FIG. 9 is an exploded perspective illustration of one adaptor embodiment with an attached interior tube which is adapted to be mounted within a suction tip as illustrated in FIG. 2.

DETAILED DESCRIPTION OF THE PREFERRED EMBODIMENTS

Figure 1:
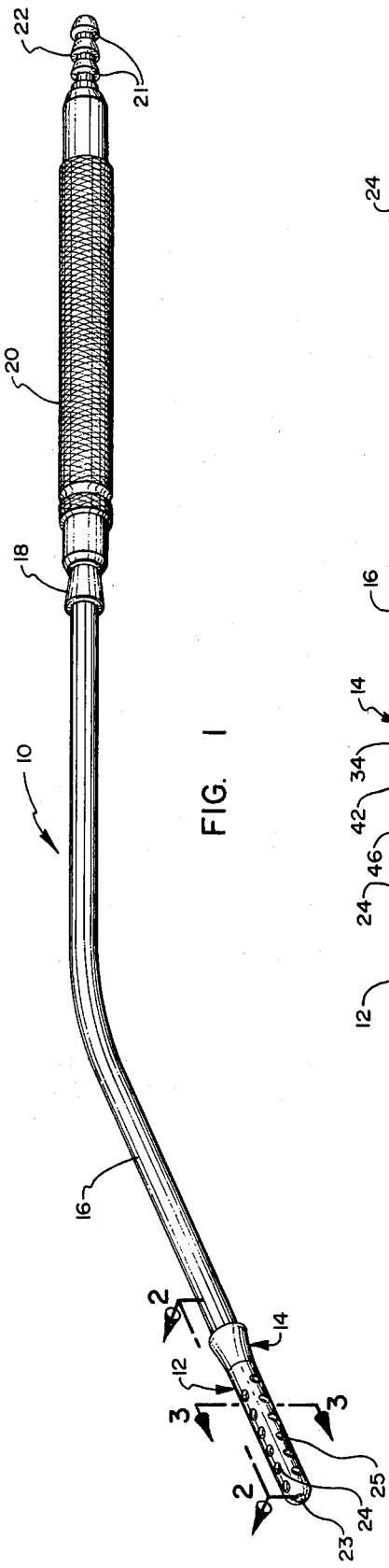
FIG. 1 is a perspective illustration of one presently preferred suction wand embodiment in assembled condition, the FIG. 1 embodiment particularly illustrating the suction tip attached to a handle.

The invention is best understood by reference to the drawing wherein like parts are designated with like numerals throughout.

Referring particularly to FIG. 1, the modular suction assembly generally designated 10 is illustrated. The assembly 10 comprises a suction tip 12, an adaptor 14, an elongated probe 16 and a handle 20. The handle 20 may be a weighted metal handle removably press-fit against the ramp surface 18 so that the trailing end 22 of the probe 16 projects beyond the handle. The trailing end 22 has a plurality of annular collars 21, to facilitate attachment to conventional suction tubing (not shown).

Figure 2:
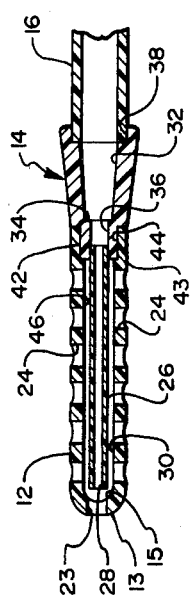
FIG. 2 is a cross section taken along lines 2—2 of FIG. 1.
Figure 4:
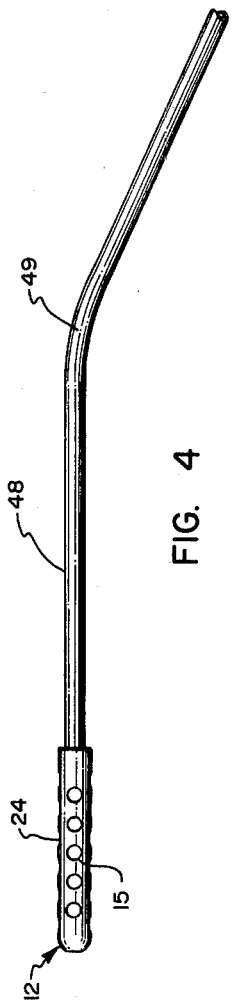
FIG. 4 is a fragmentary elevational view of another suction wand embodiment, the FIG. 4 embodiment having an adaptor which differs from the embodiment of FIG. 1.

Particular attention is now directed to the suction tip 12 which is also illustrated in FIG. 2. The suction tip 12 comprises an elongated cylindrical body having a contoured leading end 13, the contoured end 13 being rounded and smooth so that the suction tip 12 can be easily and safely inserted into a wound, surgical incision or the like. The tip 12 is preferably formed by injection molding the tip over a mandrel or core pin (not shown) which is square in cross-section. Accordingly, in the illustrated embodiment the hollow cavity 46 of the tip 12 is square in cross-section. While the illustrated embodiment is square, triangular or other suitable polygonal configuration could be used.

The square cross-sectional configuration of the cavity 46 has significant advantages. Surprisingly, each flat face of the cavity 46 permits precision forming of the apertures 24 by seating the aperture forming pins on the flat surfaces of the core pin. The importance of carefully sizing and locating the apertures 24 in the body of the tip 12 will become more fully apparent hereinafter.

Figure 3:
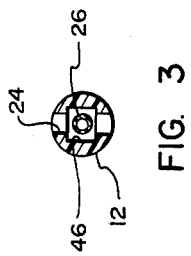
FIG. 3 is a cross section taken along lines 3—3 of FIG. 1.

It is pointed out by reference to FIG. 1 that the apertures 24 are aligned along the axis of the body 12. The apertures 25 are also aligned along the axis of the body 12 and intersect an adjacent flat face of the interior cavity 46 (see FIG. 3). Notably, the apertures 25 are spaced slightly rearwardly of the apertures 24 so that each aperture 25 is offset with respect to each aperture 24. In the tip 12, apertures are spaced into each quadrant around the body of the tip. If a triangular configuration were used, it would be desirable to align the apertures 24 and 25 so as to intersect the internal flat face of the triangular cavity (not shown). An aperture 23 is formed in the leading end of the tip 12.

The trailing end 43 of the tip 12 is provided with an annular recess or annulus 44 which is sized so as to accept any one of a plurality of adaptors to be hereinafter more fully described. For ease of illustration, adaptor 14 is shown attached to the tip 12. The adaptor 14 has an annular forwardly projecting shank 42 which nests within the annular recess 44 in press-fit relation. The attachment may be made permanent with a bonding solvent, adhesive or through any other suitable bonding technique such as ultrasonic welding. The adaptor 14 has an outwardly flaring exterior surface and a through-bore 36. The through-bore 36 tapers gradually outwardly at 32 so as to present a conventional female luer fitting. In addition, the adaptor 14 is provided with an annular recess 38 into which the leading end of cylindrical probe 16 may be mounted. Accordingly, the adaptor 14 may interchangeably receive a conventional male luer fitting or the probe 16.

If desired, the adaptor 14 may be fitted with a cylindrical tube 26 shown both in FIGS. 2 and 9. The tube 26 has a through-bore 28 and an external dimension which is sufficiently less than the internal diametral dimension of the hollow 46 of tip 12 that the tube 26 is spaced from each interior face of the cavity 46. Furthermore, the length of the tube 26 is selected so that it terminates short of the leading end 13 of the tip 12 so as to provide a space 15. In the illustrated embodiment, the tube 26 is press-fit into the shank 42 of the adaptor 14. This construction has been found to facilitate assembly and to improve the modular characteristics of the interchangeable parts of this development. However, it may also be desirable to mount the tube 26 directly to a portion of the tip 12, interior thereof.

The assembled tip 12, as described, has been found to have several surprising advantages. For example, if the tip 12 is inserted into a shallow pool of blood for aspiration, the space 15 between the tube 26 and the tip 13 will fill with blood through the aperture 23 and the blood will then be aspirated through the tube 26, adaptor 14 and subsequently the probe 16. Moreover, should the aperture 23 become obstructed with tissue fragments or the like, blood can be directed through the apertures 24 and 25 closest to the tip 13. It should be observed that obstruction of one of the apertures 23 will not clog the tip 12 so as to prevent the suction from operating on the remaining apertures. Contrary to many prior art devices, the apertures 24 and 25 provide sufficient vent that suction will not cause tissue fragments and debris to firmly lodge in the tip 12 to disable the suction tip 12.

In deeper pools of blood, blood will be aspirated through all of the apertures 23, 24 and 25 and obstruction of some of the apertures by tissue fragments or the like will not prevent aspiration of the blood through remaining apertures. It is also observed that as long as a small amount of blood is remaining to be aspirated, the tube 26 will prevent large amounts of air from being mixed with the blood as it is aspirated. The configuration of the tip 12, therefore, significantly contributes to the efficiency of the blood aspiration assembly 10.

Attention is now directed to FIGS. 4-8 which illustrate various adaptor configurations which can be advantageously used with the illustrated embodiment of the suction tip 12. Each adaptor configuration is modular in nature so that it may be selectively coupled with the suction tip 12 at the time of assembly, depending on the particular use to which the suction tip 12 will be put.

Referring more particularly to 4, the adaptor 48 is illustrated as replacing the probe 16, adaptor 14 and handle 20. The adaptor 48 is an elongated hollow substantially rigid tube having an intermediate bend 49. Preferably, the adaptor 48 is provided with a suitable coupling site to which suction tubing may be directly attached. The adaptor 48 is diametrally reduced so as to correspond directly with the diameter of the annulus 44 (see FIG. 2).

With reference to FIG. 5, an adaptor 50 is illustrated mounted to the tip 12. The adaptor 50 has a forwardly projecting annular shank (not shown) which is substantially the same as the annular shank 42 illustrated in FIGS. 2 and 9. The adaptor 50 has an external diameter which is substantially the same as the external diameter of the tip 12 so that the entire assembly presents a smooth surface. The trailing end 52 of the adaptor 50 is tapered to a smaller diameter so that conventional suction tubing 54, illustrated in broken lines in FIG. 5, may be press-fit onto the adaptor 50. The trailing end 52 also defines a female luer fitting to facilitate attachment to a vacuum source through a luer coupling.

With reference to FIG. 6, the adaptor 56 has an external diameter which conforms to the exterior of the tip 12. The adaptor 56, however, is essentially rigid and provided with a 90° bend 57 essentially midlength. The trailing end 59 of the adaptor is tapered inwardly so as to receive a tube similar to tube 54 illustrated in FIG. 5. Alternatively, the adaptor 59 may be provided with a female luer fitting substantially resembling that of adaptor 14 (FIG. 2). Thus, the adaptor 56 may receive a coupling 58 of conventional flexible tubing 60. It is observed that the tubing 60 has a comparatively small diameter and, if desired, the tapered end 62 of coupling 64 may be inserted into the tube 60 so that the tube 60 may be attached to conventionally sized suction tubing such as tubing 54 shown in FIG. 5. The angled adaptor 56 is particularly useful when the assembly is employed as a surgical sump. Surgical sump applications are particularly advantageous where prolonged aspiration of biological fluids is required.

With reference to FIG. 7, the adaptor 72 resembles closely the adaptor 56 illustrated in FIG. 6, except that the adaptor 72 has a bend 73 which is considerably less than 90° and more advantageous for some applications. As with the adaptor 56, the exterior of the adaptor 72 at the trailing end is diametrally tapered and interiorly presents a female luer fitting (not shown).

With reference to FIG. 8, the suction tip 12 is illustrated as provided with an adaptor 14, the adaptor 14 presenting a female luer fitting to receive the coupling 66 of a flexible tube 68. The trailing end of the flexible tube 68 is provided with a sizing adaptor 70 to permit the tubing 68 to be secured to the conventionally sized vacuum tubes such as tube 54 illustrated in FIG. 5.

In all of the embodiments described above, the corresponding adaptors are modular. Each adaptor has one end which has a coupling configurated to unite the adaptor with the suction tip 12. The other end of the adaptor is configurated to mate with any one of a variety of conventional medical appliances for creating vacuum at the suction tip 12. Significantly each of the adaptors has a configuration which is uniquely desirable for selected kinds of surgery whether the surgery be open-heart surgery, or for rapid evacuation of hemothorax or ascites in both adult and pediatric sizes.

The method of assembly is substantially simplified because the entire assembled unit can be constructed according to need from a variety of modular parts and, therefore, a large number of complicated dyes and injection molds are unnecessary. Furthermore, the arrangement of apertures in the suction tip is such as to provide efficient evacuation of biological fluids even though tissue fragments may be present so as to occlude some of the apertures.

Where variable amounts of blood are to be aspirated, the use of the interiorly placed tube 26 permits efficient evacuation of the small fluid amounts while at the same time minimizing the problems arising in connection with obstruction of the apertures with tissue fragments and the aspiration of disproportionate amounts of air.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A surgical suction wand and tip assembly comprising in combination:

an elongated suction tip comprising a body having a smoothly contoured exterior and an internal cavity which cavity is polygonal in cross-section, each face of the polygon defining an essentially flat interior surface within the tip;

an array of apertures in the body of the suction tip intersecting the longitudinal axis of the internal cavity and communicating the exterior of the body with the internal cavity at one of each of the flat surfaces of the polygon, the array in one surface being displaced along the axis of the tip with respect to the array in the adjacent surface;

an adaptor comprising a through-bore, a first coupling for securing the adaptor to the suction tip, a forwardly projecting hollow tube mounted concentric with the through-bore of the adaptor, said hollow tube projecting telescopically within the internal cavity of the suction tip, a second coupling differing in size from the first on the rear of the adaptor;

a wand assembly and means joining the adaptor to the wand assembly, said wand assembly comprising an essentially rigid hollow tube mounted to the second coupling of the adaptor and extending rearwardly therefrom;

a weighted handle of metal construction, the handle comprising a single axial, generally cylindrical through-bore opening at the leading end and at the trailing end of the handle, the leading end of the through-bore tapering outwardly;

an elongated conduit comprising a unitary, generally cylindrical insert having an external configuration which corresponds to the through-bore within the handle, the insert tapering outwardly at its leading end and joined at its leading end to the hollow tube mounted to the second coupling of the adaptor;

the external surface of the insert defining a diameter which is essentially the same as the diameter of the through-bore, said insert being telescopically surmounted by the handle and releasably attached thereto with a press-fit coupling, the through-bore receiving the insert in snug relationship along the entire length of the bore; and a coupling for flexible suction tubing integral and coextensive with the trailing end of the insert, said coupling projecting beyond the trailing end of the handle when the handle surmounts the insert.

2. A surgical suction wand and tip assembly as defined in claim 1 wherein said adaptor is elongated and tapered outwardly along the axis of the through-bore.

* * * * *